United States Patent
Mark et al.

(10) Patent No.: US 10,617,803 B2
(45) Date of Patent: *Apr. 14, 2020

(54) ASPIRATING CAUTERY FORCEPS

(71) Applicant: Nico Corporation, Indianapolis, IN (US)

(72) Inventors: Joseph L. Mark, Indianapolis, IN (US); Brian C. Dougherty, Terre Haute, IN (US)

(73) Assignee: Nico Corporation, Indianapolis, IN (US)

( * ) Notice: Subject to any disclaimer, the term of this patent is extended or adjusted under 35 U.S.C. 154(b) by 295 days.

This patent is subject to a terminal disclaimer.

(21) Appl. No.: 15/652,442

(22) Filed: Jul. 18, 2017

(65) Prior Publication Data
US 2017/0312404 A1    Nov. 2, 2017

Related U.S. Application Data

(63) Continuation of application No. 14/099,564, filed on Dec. 6, 2013, now Pat. No. 9,737,648, and a continuation of application No. 14/536,724, filed on Nov. 10, 2014, now Pat. No. 9,795,440.

(60) Provisional application No. 61/733,999, filed on Dec. 6, 2012.

(51) Int. Cl.
*A61B 18/14* (2006.01)
*A61M 1/00* (2006.01)

(52) U.S. Cl.
CPC ......... *A61M 1/0084* (2013.01); *A61B 18/148* (2013.01); *A61B 2018/1475* (2013.01); *A61B 2218/002* (2013.01); *A61B 2218/007* (2013.01)

(58) Field of Classification Search
CPC .......... A61B 18/148; A61B 2018/1475; A61B 2218/002; A61B 2218/007; A61M 1/0084
See application file for complete search history.

(56) References Cited

U.S. PATENT DOCUMENTS

| | | | |
|---|---|---|---|
| 2,667,682 A * | 2/1954 | Stone | A61B 17/34 27/24.2 |
| 3,920,021 A | 11/1975 | Hiltebrandt | |
| 4,487,600 A | 12/1984 | Brownlie et al. | |
| 4,738,666 A | 4/1988 | Fuqua | |
| 5,011,488 A | 4/1991 | Ginsburg | |
| 5,217,460 A * | 6/1993 | Knoepfler | A61B 17/29 606/1 |
| 5,312,400 A | 5/1994 | Bales et al. | |

(Continued)

OTHER PUBLICATIONS

PCT International Search Report and Written Opinion dated Mar. 29, 2016 for PCT/US2015/059850.

*Primary Examiner* — Michael F Peffley
(74) *Attorney, Agent, or Firm* — Kristin L. Murphy; Honigman LLP

(57) ABSTRACT

Multiple surgical devices that may be used during surgical procedures are shown and described herein. A surgical device includes an outer cannula and an inner member that has a pair of electrodes positioned at a distal end. The inner member defines an aspiration delivery channel with an opening. A handle assembly actuates the outer cannula relative to the inner member, thereby adjusting a size of the opening of the aspiration delivery channel. In another exemplary configuration, an irrigation hub is provided to deliver irrigation through the surgical device.

17 Claims, 4 Drawing Sheets

(56) References Cited

U.S. PATENT DOCUMENTS

| | | | |
|---|---|---|---|
| 5,709,224 A * | 1/1998 | Behl | A61B 18/1492 128/898 |
| 5,797,958 A * | 8/1998 | Yoon | A61B 17/122 606/139 |
| 5,893,863 A | 4/1999 | Yoon | |
| 6,254,598 B1 * | 7/2001 | Edwards | A61B 18/1206 606/41 |
| 6,355,035 B1 | 3/2002 | Manushakian | |
| 7,223,267 B2 | 5/2007 | Isola et al. | |
| 7,293,562 B2 | 11/2007 | Malecki | |
| 9,155,587 B2 | 10/2015 | Willis | |
| 2004/0153505 A1 | 8/2004 | West et al. | |
| 2011/0022048 A1 | 1/2011 | Bacher | |

\* cited by examiner

ASPIRATING CAUTERY FORCEPS

CROSS-REFERENCE TO RELATED APPLICATIONS

This is a continuation application of U.S. Ser. No. 14/099,564 filed Dec. 6, 2013, now U.S. Pat. No. 9,737,648 issued Aug. 22, 2017, which claims the benefit of U.S. provisional application Ser. No. 61/733,999 filed Dec. 6, 2012, and a continuation of U.S. Ser. No. 14/536,724 filed Nov. 10, 2014, now U.S. Pat. No. 9,795,440 issued Oct. 24, 2017, the disclosures of which are hereby incorporated in their entirety by reference herein.

TECHNICAL FIELD

The present disclosure relates to surgical devices that provide cauterization.

BACKGROUND

Monopolar devices have been well-known to cauterize vessels and cut tissue depending on the frequency used. Monopolar devices operate by using the patient as the ground pathway to complete the circuit. However, this arrangement is not efficacious in certain surgical applications, as the energy moves through the entire body.

Bipolar cautery devices have also been employed to coagulate and cauterize tissues. Bipolar cautery devices utilize two electrodes, with the intent to localize energy between the two poles of the electrodes, thereby minimizing energy delivery to adjacent tissues and structures. More specifically, during electrosurgical procedures, a high-frequency electric current is generated and applied to biological tissue. The electric current heats the tissue to coagulate blood vessels to reduce or stop bleeding.

However, one of the issues with bipolar cautery devices is the ability to control the amount of energy to be delivered to accomplish the desired coagulation. Less energy is required the closer the electrodes are positioned together. In certain instances, for example in neurosurgical applications, it is desirable to deliver as low an amount of energy as possible when attempting to mitigate a bleeding vessel to prevent tissue damage, especially around critical structures in the brain. However for bi-polar cautery devices where the poles are at a fixed distance apart from one another, the amount of energy for a given application can be too great for the intended target, thereby leading to undesirable collateral tissue damage.

One type of bipolar coagulation device includes bipolar forceps, whereby the two electrodes may be selectively varied in distance from one another by the user. However, care must be taken to ensure that the electrodes do not contact each other directly, as when this happens, no energy is being delivered to the intended tissues and no coagulation/cautery occurs to the intended tissue. In contrast, if the electrodes are spaced too far apart, more energy is required to achieve coagulation, which can lead to collateral tissue damage. Thus, there is a need to provide some degree of control over the spacing of the electrodes, while still permitting variability to address the specific surgical applications.

It is also known to irrigate the surgical field while using a cautery device. For example, in some known arrangements, a fluid delivery device, separate from the coagulation device, is arranged to drip irrigant into the surgical field. However, this arrangement has some drawbacks in that it is difficult to position the irrigation supply to be directly over the area of interest, and often requires an additional person in the surgical field to deliver the fluid. Moreover, the additional irrigation delivery device often impedes visibility of the surgical field. For example, in minimally invasive microsurgical procedures, the surgical corridor and the subsequent target is relatively small, thus an external drip presents delivery challenges for the additional person and visibility challenges for the surgeon whom is using the coagulation device on the intended tissue to be coagulated due to too many instruments and hands in the surgical field simultaneously. As a result, visualization at the surgical site may be compromised.

In other known devices, a separate fluid delivery conduit may be positioned above or below the forceps to provide irrigation to the surgical field. While these arrangements avoid the need for an additional person to hold and direct the irrigation supply, the fluid delivery conduit outlet is not positioned close enough to the cautery tips, but instead proximal of the electrode tips such that the fluid is not delivered to the surgical site, where the tips of the electrodes are positioned.

In addition to fluid delivery, during a surgical procedure, it is often necessary to clear the surgical field to enable the surgeon to properly visualize the field. More specifically, at times during a surgical procedure it is necessary to aspirate blood and irrigant out of the surgical field. While separate aspirating wands are known, the use of a separate surgical tool in a narrow surgical corridor can be problematic.

BRIEF DESCRIPTION OF THE DRAWINGS

Exemplary embodiments of the present disclosure will now be described in greater detail with reference to the attached figures, in which.

DETAILED DESCRIPTION

Figure 1A:
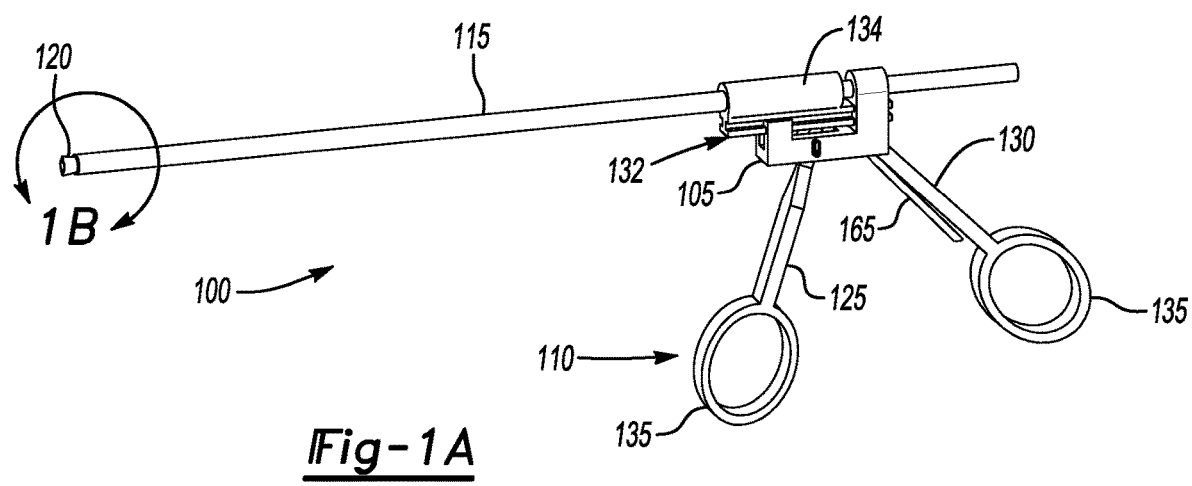
FIG. 1A illustrates an exemplary surgical device in an open position.

Referring now to the discussion that follows and also to the drawings, illustrative approaches to the disclosed instruments and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein are exemplary arrangements of cautery surgical instruments that are configured for aspiration. In addition, in one exemplary arrangement, the cautery surgical instrument also provides for delivery of fluid to the surgical field.

The surgical instrument may be configured to connect to an existing vacuum source. The vacuum supply may supply a predefined level of vacuum to a distal end of the surgical instrument. The surgical instrument may be configured to include an aspiration control device configured to selectively control the delivery of vacuum supplied to a distal end of the surgical device, including while in operation in the surgical field.

In one exemplary arrangement, a surgical device includes an outer cannula and an inner member having a pair of electrodes positioned at a distal end thereof. The inner member further includes an aspiration delivery channel having an opening at the distal end. A handle is configured to actuate the outer cannula relative to the inner member to adjust a size of the opening of the aspiration delivery channel, as well as the position of the electrodes with respect to each other. In another exemplary arrangement, the surgical device further includes a fluid delivery system. In yet a further exemplary arrangement, the surgical device also includes a mechanism configured to selectively rotate the inner member.

The Figures illustrate exemplary surgical devices, namely a pair of cautery forceps. The surgical devices may take many different forms and include multiple and/or alternate components and facilities. While exemplary forceps are shown in the Figures, the exemplary components illustrated in the Figures are not intended to be limiting. Indeed, additional or alternative components and/or implementations may be used.

Referring to FIGS. 1A-1D, an exemplary surgical device 100 is illustrated. Surgical device 100 is configured as cautery forceps and includes a support member 105, a handle assembly 110, an outer cannula 115, and an inner member 120. The handle assembly 110 may include a first arm 125 and a second arm 130, at least one of which is configured to move relative to the other in, e.g., a scissor action, to be explained in further detail below. The first arm 125 and second arm 130 may each include a finger loop 135 configured to receive a user's finger to facilitate movement of the second arm 130 relative to the first arm 125.

Operatively connected to the support housing 105 is a rail 132. In one exemplary arrangement, rail 134 includes a key member 136 that is received within a mating opening in the support housing 105. Rail 132 is configured to slide with respect to the support housing 105, when the handle assembly 110 is actuated. Supported on rail 132 is an outer cannula mount 134. Outer cannula mount 134 is fixedly connected to rail 132 such that when rail 132 moves, outer cannula mount 134 also moves. Outer cannula mount 134 includes a passage therethrough. A proximal end (not shown) of the outer cannula 115 is fixedly mounted in the passage of the outer cannula mount 134.

The outer cannula 115 may be configured to be a generally hollow, rigid tube. The outer cannula 115 is configured to move with respect to the support member 105 in response to actuation of the handle assembly 110. More specifically, the outer cannula 115 may translate between an "open" position and a "closed" position, as will be explained in further detail below.

The inner member 120 is positioned within the outer cannula 115 such that the inner member 120 and outer cannula 115 are coaxial. In one exemplary approach, the inner member 120 includes a generally hollow tube that may be configured to deliver aspiration to a surgical site.

Figure 1B:
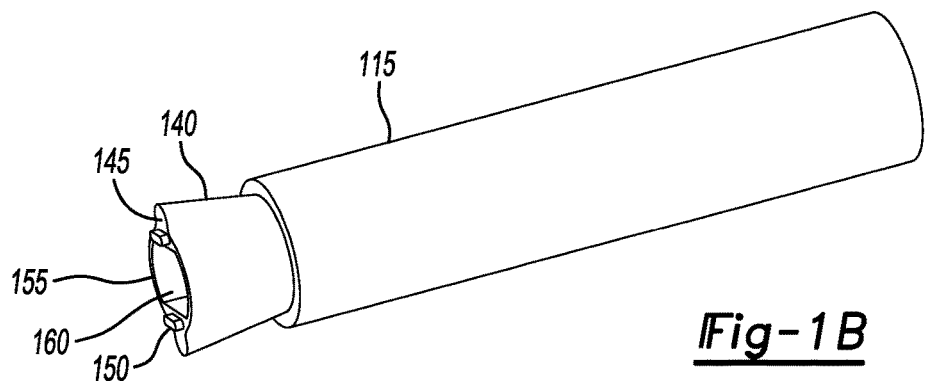
FIG. 1B is an enlarged view of encircled area 1B in FIG. 1A of the distal end of the surgical device in FIG. 1A.

As shown in FIG. 1B, the inner member 120 further includes a tip member 140 at a distal end of the inner member 120 that is configured to extend both radially and distally beyond the distal end 142 of outer cannula 115, with the position of the tip member 140 being dependent upon the position of the handle 110, as will be explained in further detail below. The tip member 140 further includes a pair of land members 145 of increased wall thickness integrally formed on opposite sides of the inner member 120. The inner member 120 further includes a pair of electrodes 150 that are configured to deliver an electric current therebetween for surgical purposes. The electrodes 150 are embedded in the wall that defines the tubular inner member 120 approximately 180 degrees apart. In one possible approach, each electrode 150 may be located near one of the land members 145. An aspiration delivery channel 155 is defined by the inner member 120 between the land members 145. The aspiration delivery channel 155 may facilitate the removal of biological material and fluids from a surgical site using, e.g., vacuum pressure. Each electrode 150 may be embedded into the inner member 120 on opposite sides of the aspiration delivery channel 155. Proximal ends (not shown) of the electrodes 150 may be configured to extend proximally of the support member 105 and operatively connect to an electrical connector to supply power to the electrodes in a conventional manner.

In one possible implementation, tip member 140 may be formed from a flexible material, such as silicone or another suitable material. The tip member 140 is fixed connected to the inner member 120 such that the opening of aspiration delivery channel 155 formed in the tip member 145 aligns with the aspiration delivery channel 155 formed through the inner member 120. The tip member 140 may operate to insulate the electrodes 150 from one another and from the outer cannula 115.

In one exemplary arrangement, the inner member 120 extends proximally through the outer cannula mount 134 and through the support member 105. A proximal end of the inner member 120 may be connected to a vacuum supply device (not shown) via suitable tubing.

Operation of the surgical device 100 will now be described. When surgical device 100 is in the open position (shown in FIGS. 1A-1B), the first arm 125 is in a distal position such that finger loop 135 of first arm 125 is angled away from finger loop 135 of second arm 130, toward the distal end of the surgical device. First arm 125 is pivotally mounted to the support member 105 but has and end portion operatively connected to the rail 132. When the first arm 125 is positioned in the open position, the rail 132 is forced in the proximal direction such that the outer cannula mount 134, which is fixed to the rail 132, is forced toward a proximal end of the support member 105. Because the outer cannula 115 is fixed to the outer cannula mount 134, the outer cannula 115 will also move in the proximal direction, thereby exposing the tip member 145 of the inner member 120. When the outer cannula 115 is moved to its proximal-most position, the flexible tip member 145 will be permitted to expand radially outwardly, as shown in FIG. 1B. In the open position configuration, the electrodes 150 are spaced the furthest apart.

Figure 1C:
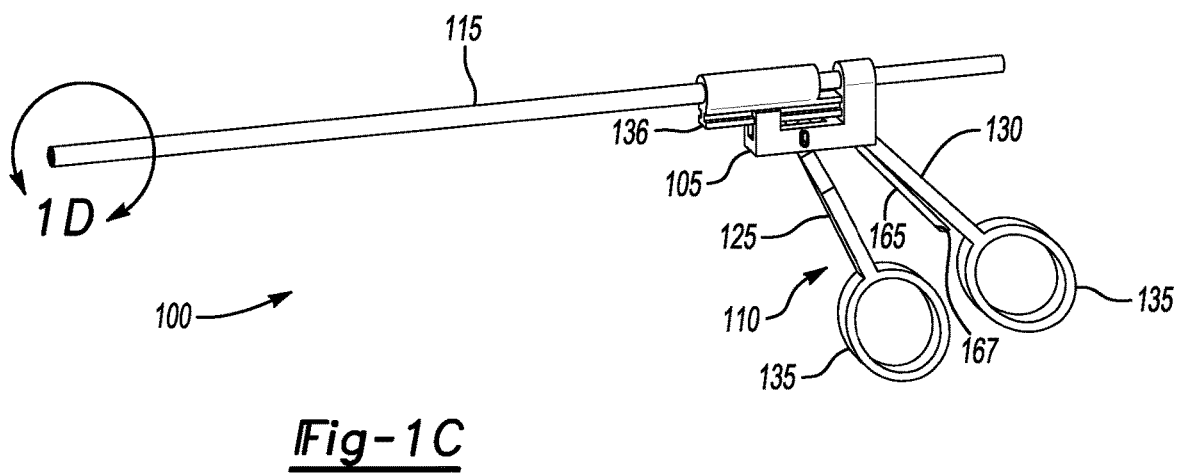
FIG. 1C illustrates the surgical device of FIG. 1A in a closed position.
Figure 1D:
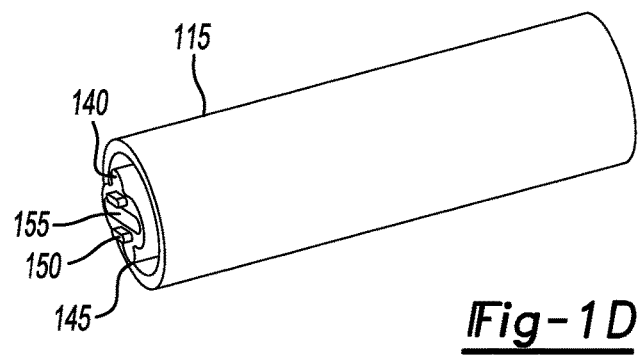
FIG. 1D is an enlarged view of the encircled area 1D in FIG. 1C of the distal end of the surgical device in FIG. 1C.

To increase the amount of energy to be delivered to tissue, the surgical device 100 may be moved from the open position toward a closed position, as shown in FIGS. 1C-1D, such that the electrodes 150 may be moved closer together. More specifically, as demonstrated in FIG. 1C, the first arm 125 is pivoted toward the second arm 130, such that the finger loop 135 of the first arm 125 is moved toward the finger loop 135 of the second arm 130. This action causes the rail 132 (carrying the outer cannula mount 134 thereon) to move in the distal direction. The outer cannula 115 that is fixedly mounted to the outer cannula mount 134 is thereby moved over the tip member 140.

As best seen in FIG. 1D, as the outer cannula 115 moves over the tip member 140, due to the flexible nature of the tip member 140, the tip member 140 becomes compressed within the outer cannula 115. The compression of the tip member 140 thereby serves to move the electrodes 150 closer together, as well as narrowing the aspiration delivery channel 155 as compared to the open position configuration of the aspiration delivery channel 155. Thus, the present arrangement of the surgical device allows flexibility in the amount of energy to be delivered to the surgical site by the electrodes 150, by a controlled movement of the first arm member 125. Moreover, the present arrangement also allows for some predictability in the amount of energy to be delivered, in that the fully opened position is fixed by the complete retraction of the outer cannula 115 in the proximal direction and the fully closed position is fixed by the outer cannula 115 completely compressing the tip member 140. The aspiration delivery channel 115 remains open, even when the tip member 140 is fully compressed, thereby providing both aspiration to the surgical site, but also maintaining the electrodes 150 apart. In one exemplary arrangement, in the fully compressed position, a gap of approximately 0.75 mm is provided between the electrodes 150.

The exemplary configuration of the aspiration delivery channel 155 also provides that an opening 160 thereto has a selectively adjustable size. Indeed, due to the flexibility of the tip member 140, the size of the opening 160 of the aspiration delivery channel 155 may change by pinching the periphery of opening 160 due to the land members 145 movement toward one another as the outer cannula 115 is slid over the inner member 120. For example, as shown in FIG. 1D, to pinch the opening 160, the outer cannula 115 is pushed toward the distal end of the inner member 120 as the first arm 125 is pivoted toward the second arm 130. The increased thickness of the tip member 140 of the inner member 120 created by the land members 145 causes the outer cannula 115 to pinch the opening 160 of the aspiration delivery channel 155, thus reducing its size, as the second arm 130 moves toward the "closed" position. Moreover, intermediate positions between the "open" position and "closed" position can be used to control the size of the opening 160 of the aspiration delivery channel 155.

As shown in FIGS. 1C and 1D, the opening 160 is largest when the handle 110 is in the "open" position and narrowest when in the "closed" position, respectively, because the outer cannula 115 exerts more force on the inner member 120 when in the "closed" position than when in the "open" position due to the shape and configuration of the land members 145. Moving the second arm 130 to a location between the "open" position and the "closed" position may cause the outer cannula 115 to apply an intermediate force to the inner member 120. The ability to apply intermediate amounts of force to the inner member 120, and thus control the size of the opening 160, may allow the physician or other use to selectively apply different amounts of aspiration during the surgical procedure.

In operation, the outer cannula 115 may move in a first (e.g., distal) direction to act on the inner member 120, which as discussed above delivers the aspiration and includes the two electrodes 150. When the outer cannula 115 is moved in the first direction by, e.g., the scissor action of the first and second arms 125, 130, the electrodes 150 move closer to each other to maximize the effect of coagulation on a specific intended, and localized, vessel, which may be drawn toward the aspiration delivery channel 155.

In some instances, it may be desired to turn off the aspiration delivery at the tip member 140. For example, for tissue that was drawn to the opening 160, it may be necessary to release the tissue to reposition the surgical device. To accomplish this task and aspiration vent tube 165 is provided. In one exemplary arrangement, the vent tube 165 is fluidly connected to the aspiration delivery channel 155 in the inner member 120 and extends downwardly from the support member 150. The vent tube 165 includes an opening 167 that may be selectively covered to provide vacuum, and selectively uncovered to vent vacuum from the aspiration delivery channel 155. In one exemplary arrangement, the vent tube 165 is positioned adjacent the second arm 130 there by permitting the surgeon to grip both the finger loop 135 of the second arm 130 and cover the opening 167 in the vent tube 165 with a single hand. While the surgical device 100 has been described as including a vent tube 165, it is understood that such an arrangement is optional. Moreover, other configurations for selectively venting or turning off the vacuum being delivered to the surgical site. For example, the vacuum delivery device to which the inner member 120 is connected may be operatively connected to a foot pedal that may be toggled on and off.

Referring now to FIGS. 2A-2D, another exemplary arrangement of a surgical device 200 configured as cautery forceps is illustrated. Surgical device 200 is similar to surgical device 100 in that it includes a support member 205, a handle assembly 210, an outer cannula 215 and an inner member 220. The handle assembly 210 may include a first arm 225 and a second arm 230, at least one of which is configured to move relative to the other in, e.g., a scissor action, to be explained in further detail below. The first arm 225 and second arm 230 may each include a finger loop 235 configured to receive a user's finger to facilitate movement of the second arm 230 relative to the first arm 225, as will be explained in further detail below.

Operatively connected to the support housing 205 is a rail 232. In one exemplary arrangement, rail 234 is configured as a key member that is received within a mating opening in the support housing 205. Rail 232 is configured to slide with respect to the support housing 205, when the handle assembly 210 is actuated. Supported on rail 232 is an outer cannula mount 234. Outer cannula mount 234 is fixedly connected to rail 232 such that when rail 232 moves, outer cannula mount 234 also moves. Outer cannula mount 234 includes a passage 236 (best seen in FIG. 2C) therethrough. A proximal end 238 of the outer cannula 215 is fixedly mounted in the passage of the outer cannula mount 234.

The outer cannula 215 may be configured to be a generally hollow, rigid tube. The outer cannula 215 is configured to move with respect to the support member 205 in response to actuation of the handle assembly 210. More specifically, the outer cannula 215 may translate between an "open" position and a "closed" position, as will be explained in further detail below.

The inner member 220 is positioned within the outer cannula 215 such that the inner member 220 and outer cannula 215 are coaxial. In one exemplary approach, the inner member 220 includes a generally hollow tube that may be configured as an aspiration delivery channel 252 to deliver aspiration to a surgical site. A proximal end 242 of the inner member 220 is configured to mate with an aspiration supply assembly 244.

The inner member 220 is also configured with electrode channels 254 (best seen in FIG. 2D) that are positioned within the wall of the inner member 220. The electrode channels 254 are configured to be larger than electrodes 250 positioned therein so as to create an annular space around the electrodes 250, as will be explained in further detail below.

Figure 2A:
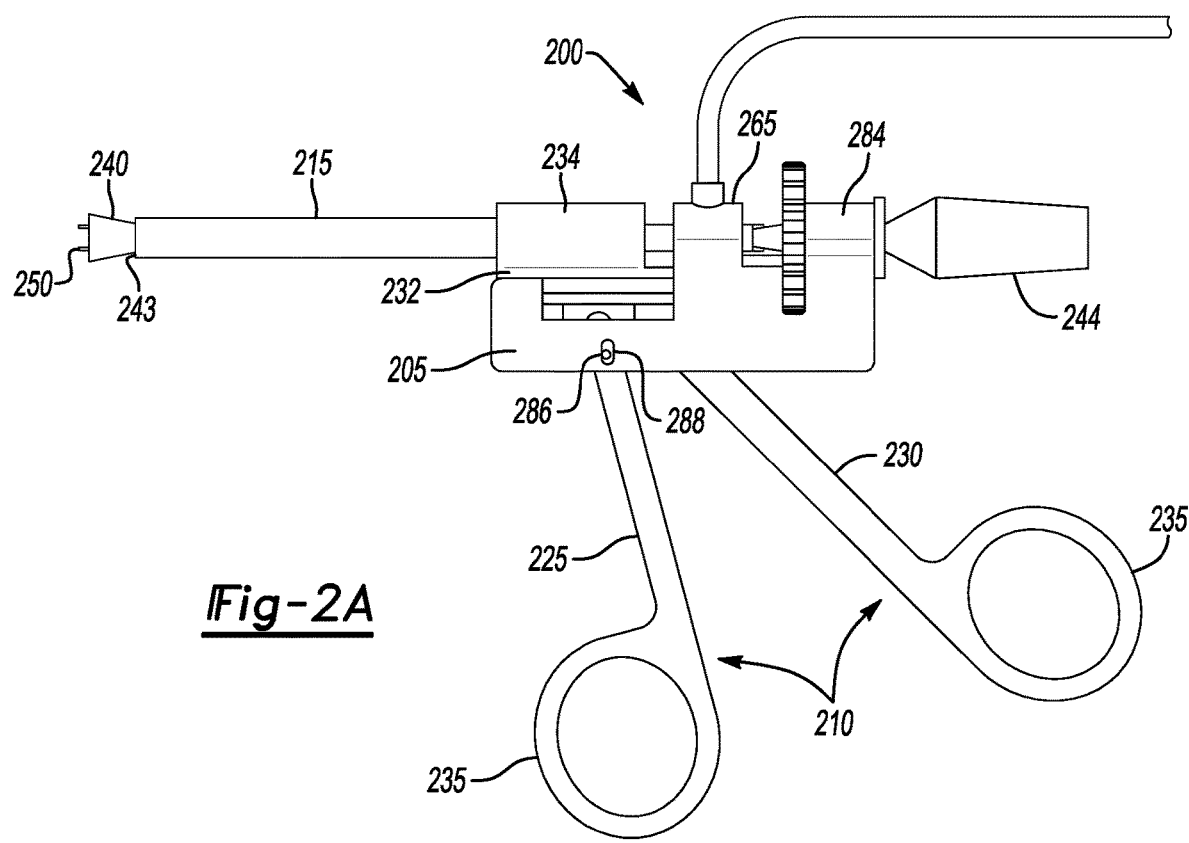
FIG. 2A illustrates an elevational view of an alternative arrangement of the surgical device of FIGS. 1A-1D.
Figure 2B:
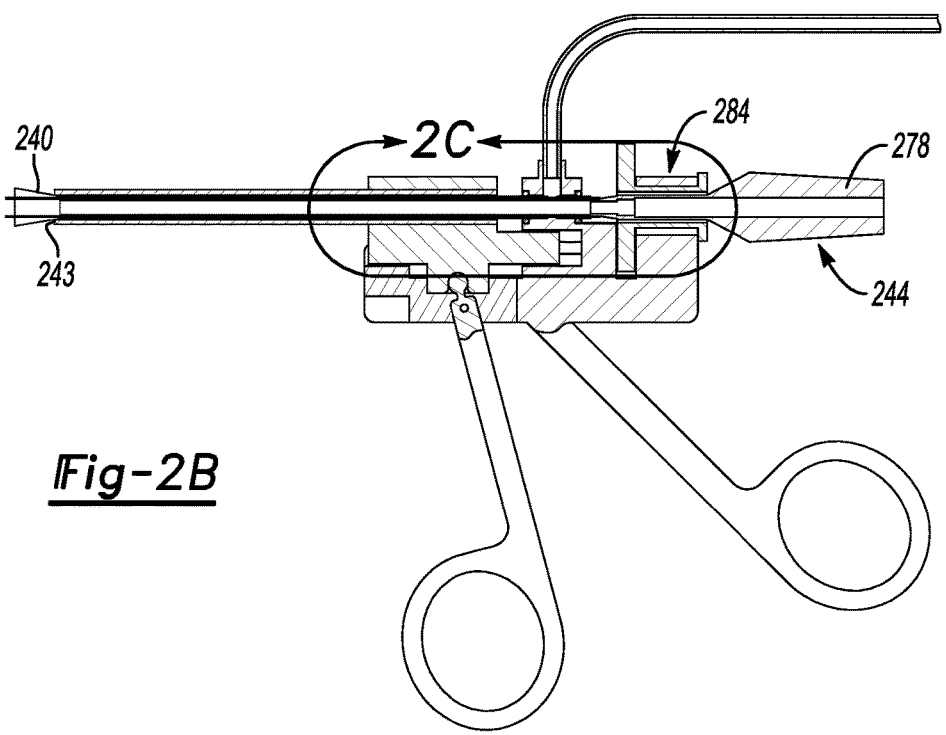
FIG. 2B illustrates a cross-sectional view of the surgical device of FIG. 2A.
Figure 2C:
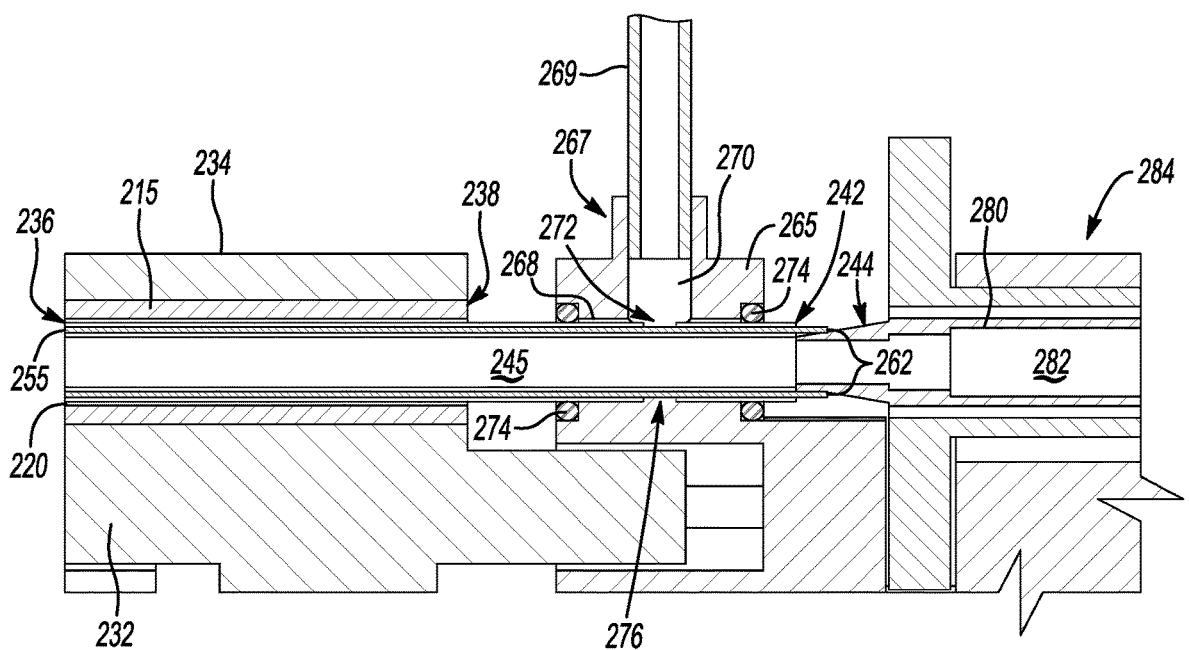
FIG. 2C is an enlarged view of the encircled area 2C in FIG. 2B.
Figure 2D:
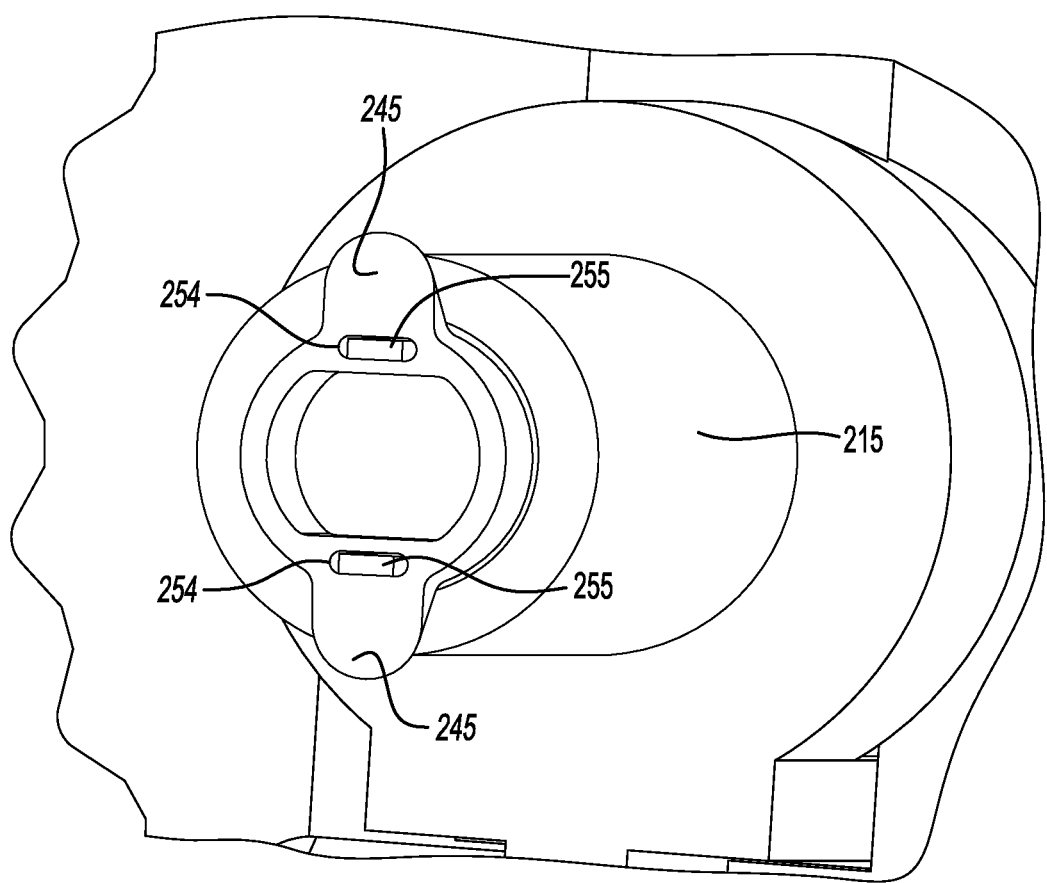
FIG. 2D is an enlarged perspective view of a distal end of the surgical device of FIG. 2A.

As shown in FIG. 2B, the inner member 220 further includes a tip member 240 at a distal end of the inner member 220 that is configured to extend both radially and distally beyond a distal end 243 of outer cannula 215, with the position of the tip member 240 being dependent upon the position of the handle assembly 210, as will be explained in further detail below. As best seen in FIG. 2C, the tip member 240 further includes a pair of land members 245 of increased wall thickness integrally formed on opposite sides of the inner member 220, similar that which was described above in connection with the arrangement shown in FIGS. 1A-1D. The inner member 220 further includes a pair of electrodes 250 that are configured to deliver an electric current therebetween for surgical purposes. The electrodes 250 are positioned in the electrode channels 254 formed in the wall that defines the tubular inner member 220 approximately 180 degrees apart. In one possible approach, each electrode 250 may be located near one of the land members 245. An opening 260 to an aspiration delivery channel 255 is defined by the inner member 220 between the land members 245. The aspiration delivery channel 255 may facilitate the removal of biological material and fluids from a surgical site using, e.g., vacuum pressure. Proximal ends 262 of the electrodes 250 may be configured to extend proximally of the inner member 220 and operatively connect to an electrical connector to supply power to the electrodes in a conventional manner. In one exemplary arrangement, a connector element (not shown) may be positioned over the proximal ends 262 of the electrodes 250 to establish a connection between a power source, as well as serving as a mount for a distal end of the aspiration supply connector assembly 244.

In one possible implementation, tip member 240 may be formed from a flexible material, such as silicone or another suitable material. The tip member 240 is fixedly connected to the inner member 220 such that the opening 260 of aspiration delivery channel 255 formed in the tip member 245 aligns with the aspiration delivery channel 255 formed through the inner member 220. The tip member 240 may operate to insulate the electrodes 250 from one another and from the outer cannula 215.

Turning to FIG. 2C, the support member 205 further includes an irrigation hub 265 attached thereto. In one exemplary configuration the irrigation hub 265 is integrally connected to support member 205. Irrigation hub 265 includes a fitting member 267 that is configured to connect to suitable tubing 269 and a passageway 268 into which the inner member 220 extends. The fitting member 267 is in communication with a channel 270 that opens into notches 272 formed through the inner member 220 disposed within the passageway 268. The notches 272 are in communication with the electrode channels 254.

Sealing grooves are disposed distally and proximally of the fitting member 267, adjacent to the openings of the passageway 268. The sealing grooves each receive a sealing member 274, such as an O-ring. The sealing members 274 cooperate with the outside surface of the inner member 220 to define an irrigation chamber 276 within the irrigation hub 265.

The aspiration supply connector assembly 244 includes an aspiration connector element 278 and an aspiration cannula 280 extending distally from the aspiration connector element 278. The aspiration connector element 278 may be partially received within the proximal end 242 of the inner member 220 in a frictional engagement, or the distal end of the aspiration connector element 278 may be glued or otherwise fixedly connected to the proximal end 242 of the inner member 220. In this manner, the aspiration delivery channel 245 aligns with and is in communication with a channel 282 formed in the aspiration cannula 280.

In one exemplary arrangement, a wheel hub 284 is provided. Wheel hub 284 is disposed on the support member 205, but configured for rotational movement with respect to the support member 205. The wheel hub 284 defines a passageway therethrough. The aspiration cannula 280 extends through the wheel hub 284 and is fixedly secured thereto. In this manner, when the wheel hub 284 is selectively rotated, the aspiration cannula 280 also rotates. Moreover, when the aspiration cannula 280 is secured to the inner member 220, rotation of the wheel hub 284 will also rotate the inner member 220, including tip member 240 secured thereto.

Operation of the surgical device 200 will now be described. When surgical device 200 is in the open position (shown in FIGS. 2A and 2B), the first arm 225 is in a distal position such that finger loop 235 of first arm 225 is angled away from finger loop 235 of second arm 230, toward the distal end of the surgical device. First arm 225 is pivotally mounted to the support member 205 but has and end portion operatively connected to the rail 232. When the first arm 225 is positioned in the open position, the rail 232 is forced in the proximal direction such that the outer cannula mount 234, which is fixed to the rail 232, is forced toward a proximal end of the support member 205. More specifically, a pin member 286 interacts with a groove 288 formed on the support member 205 to force the outer cannula mount 234 to move proximally. Because the outer cannula 215 is fixed to the outer cannula mount 234, the outer cannula 215 will also move in the proximal direction, thereby exposing the tip member 245 of the inner member 220. When the outer cannula 215 is moved to its proximal-most position, the flexible tip member 245 will be permitted to expand radially outwardly, as shown in FIG. 2B. In the open position configuration, the electrodes 250 are spaced the furthest apart.

To increase the amount of energy to be delivered to tissue, the surgical device 200 may be moved from the open position toward a closed position, similar to that as shown in FIGS. 1C-1D, such that the electrodes 250 may be moved closer together. More specifically, the first arm 225 is pivoted toward the second arm 230, such that the finger loop 235 of the first arm 225 is moved toward the finger loop 235 of the second arm 230. This action causes the rail 232 (carrying the outer cannula mount 234 thereon) to move in the distal direction. The outer cannula 215 that is fixedly mounted to the outer cannula mount 234 is thereby moved over the tip member 240.

As the outer cannula 215 moves over the tip member 240, due to the flexible nature of the tip member 240, the tip member 240 becomes compressed within the outer cannula 215. The compression of the tip member 240 thereby serves to move the electrodes 250 closer together, as well as narrowing the aspiration delivery channel 255 as compared to the open position configuration of the aspiration delivery channel 255. Thus, the present arrangement of the surgical device allows flexibility in the amount of energy to be delivered to the surgical site by the electrodes 250, by a controlled movement of the first arm member 225. Moreover, the present arrangement also allows for some predictability in the amount of energy to be delivered, in that the fully opened position is fixed by the complete retraction of the outer cannula 215 in the proximal direction and the fully closed position is fixed by the outer cannula 215 completely compressing the tip member 240. The aspiration delivery channel 215 remains open, even when the tip member 240 is fully compressed, thereby providing both aspiration to the surgical site, but also maintaining the electrodes 250 apart.

The exemplary configuration of the aspiration delivery channel 255 also provides that the opening 260 thereto has a selectively adjustable size. Indeed, due to the flexibility of the tip member 240, the size of the opening 260 of the aspiration delivery channel 255 may change by pinching the periphery of opening 260 due to the land members 245 movement toward one another as the outer cannula 215 is slid over the inner member 220. More specifically, the increased thickness of the tip member 240 of the inner member 220 created by the land members 245 causes the outer cannula 215 to pinch the opening 260 of the aspiration delivery channel 255, thus reducing its size, as the second arm 230 moves toward the "closed" position. Moreover, intermediate positions between the "open" position and "closed" position can be used to control the size of the opening 260 of the aspiration delivery channel 255.

The opening 260 is largest when the handle 210 is in the "open" position and narrowest when in the "closed" position, respectively, because the outer cannula 215 exerts more force on the inner member 220 when in the "closed" position than when in the "open" position due to the shape and configuration of the land members 245. Moving the second arm 230 to a location between the "open" position and the "closed" position may cause the outer cannula 215 to apply an intermediate force to the inner member 220. The ability to apply intermediate amounts of force to the inner member 220, and thus control the size of the opening 260, may allow the physician or other use to selectively apply different amounts of aspiration during the surgical procedure.

In operation, the outer cannula 215 may move in a first (e.g., distal) direction to act on the inner member 220, which as discussed above delivers the aspiration and includes the two electrodes 250. When the outer cannula 215 is moved in the first direction, the electrodes 250 move closer to each other to maximize the effect of coagulation on a specific intended localized, vessel, which may be drawn toward the aspiration delivery channel 255.

In some instances, it may be desirable to rotate the tip member 240. More specifically, to access a particular vessel or other structure within the surgical site, it may be necessary to change the orientation of the tip member 240 to avoid the land member 245. Rather than require the surgeon to execute uncomfortable manipulation of the surgical device 200, the surgeon can simply rotate the wheel hub 284 to properly orient the surgical device.

In some instances, it may be necessary to irrigate the surgical field. Rather than require a separate device to attempt to deliver irrigant to the desired location adjacent the electrode tips 250, the present surgical device 200 provides for irrigant to be delivered through the irrigation hub 265 from a suitable irrigant supply tubing 269 through the electrode channels 254 (best seen in FIG. 2D). By delivering the fluid through the electrode channels 254, fluid is delivered to the proper location at the surgical field, without compromising visibility during the procedure. To prevent irrigant from flowing out the proximal end 242 of the inner member 220, the annular space may be sealed at the proximal end 242.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

What is claimed is:

1. A surgical device comprising:
   a rigid outer cannula;
   an inner member disposed within the outer cannula and having a pair of electrode channels formed within the inner member, each channel being spaced apart from one another and having an electrode disposed therein, the inner member having an unsplit compressible tip member that defines a distal end of the inner member, the electrodes extending from the distal end of the inner member, wherein the inner member defines an aspiration delivery channel having an opening at the distal end of the inner member, the electrodes not being exposed within the aspiration delivery channel due to the electrode channels; and
   a selectively actuatable handle assembly connected to the outer cannula, the handle assembly configured to move the outer cannula distally over the inner member to selectively move the electrodes toward one another.

2. The surgical device of claim 1, wherein the surgical device is selectively configurable between an open position and a closed position, wherein, the compressible tip member has an outer diameter greater than a diameter of the outer cannula when in the open position, such that the tip member extends radially outwardly from a distal end of the outer cannula, and wherein in the closed position, the tip member is at least partially compressed within the outer cannula.

3. The surgical device of claim 1, wherein the tip member further includes a pair of land members.

4. The surgical device of claim 3, wherein the pair of electrodes is positioned in a wall thickness that defines the tip member, adjacent the land members.

5. The surgical device of claim 3, wherein the land members are separated by the opening to the aspiration delivery channel.

6. The surgical device of claim 1, wherein a proximal end of the inner member is configured to be operatively attached to a vacuum supply source.

7. The surgical device of claim 1, further comprising a vent tube in communication with the aspiration delivery channel, wherein the vent tube is configured to selectively relieve vacuum pressure from the aspiration delivery channel.

8. The surgical device of claim 1, wherein the inner member is defined by a wall thickness, and wherein the pair of electrode channels are disposed within the wall thickness.

9. A surgical device comprising:
an outer cannula;
an inner member disposed within the outer cannula and having a pair of electrodes embedded within a wall of the inner member such that the electrodes are axially fixed with respect to the inner member, the electrodes extending from a distal end of the inner member, wherein the inner member defines an aspiration delivery channel having an opening at the distal end of the inner member;
a selectively actuatable handle assembly connected to the outer cannula, the handle assembly moving the outer cannula over the inner member to selectively move the electrodes toward one another; and
a wheel hub, wherein the wheel hub is mounted for fixed rotational movement with the inner member, such that rotation of the wheel hub rotates the inner member with respect to the outer cannula.

10. The surgical device of claim 9, further comprising an aspiration supply connector operatively connected to a proximal end of the inner member.

11. The surgical device of claim 9, further comprising
a support member, and wherein the outer cannula is fixedly mounted to a rail member, wherein the
handle assembly is configured to move the rail member with respect to the support member to move the outer cannula over the inner member.

12. The surgical device of claim 11, further comprising
a tip member constructed of a flexible material, the tip member defining the distal end of the inner member, wherein the tip member is defined by a wall thickness, and wherein the tip member further includes a pair of land members having an increased wall thickness as compared to a remainder of the tip member, wherein the land members are arranged in an opposing manner.

13. The surgical device of claim 9, wherein the electrode channels are sized to be larger than the electrodes to create an annular gap between the electrodes and inner surface of the electrode channels.

14. The surgical device of claim 13, further comprising an irrigation hub that is in communication with the electrode channels, wherein the irrigation hub is configured to be operatively connected to an irrigation supply to deliver irrigation through the electrode channels.

15. The surgical device of claim 14, wherein the irrigation hub further comprises a fitting member that is configured to connect to the irrigation supply, a passageway into which the inner member extends, and a channel that is in communication with the fitting member and with notches formed through the inner member that are in communication with the electrode channels.

16. The surgical device of claim 15, further comprising sealing members disposed distally and proximally of the notches, wherein the sealing members cooperate with the inner member to define a sealed irrigation chamber within the irrigation hub.

17. A surgical device comprising:

an outer cannula;

an inner member disposed within the outer cannula and having a pair of electrode channels formed within the inner member, each channel being spaced apart from one another and having an electrode disposed therein, the electrode channels are sized to be larger than the electrodes to create an annular gap between the electrodes and an inner surface of the electrode channels, the inner member having an unsplit compressible tip member that defines a distal end of the inner member, the electrodes extending from the distal end of the inner member, wherein the inner member defines an aspiration delivery channel having an opening at the distal end of the inner member, the electrodes not being exposed within the aspiration delivery channel due to the electrode channels; and a selectively actuatable handle assembly connected to the outer cannula, the handle assembly configured to move the outer cannula distally over the inner member to selectively move the electrodes toward one another.

* * * * *